United States Patent [19]

Pokora et al.

[11] Patent Number: 5,110,740
[45] Date of Patent: May 5, 1992

[54] PRETREATMENT OF PHENOLIC RESIN SUSPENSION TO REMOVE RESIDUAL PHENOL

[75] Inventors: Alexander R. Pokora, Pickerington, Ohio; John J. Stolfo, Lenox, Mass.

[73] Assignee: The Mead Corporation, Dayton, Ohio

[21] Appl. No.: 403,530

[22] Filed: Sep. 6, 1989

[51] Int. Cl.$^5$ .................... C07B 63/00; B41M 5/20; B32B 7/04; C12P 7/00
[52] U.S. Cl. .................... 435/262; 503/225; 428/420; 435/132
[58] Field of Search ................ 435/262, 132; 503/225; 428/420

[56] References Cited

U.S. PATENT DOCUMENTS

| | | | |
|---|---|---|---|
| 3,871,964 | 3/1975 | Hüper et al. | 435/262 |
| 4,173,684 | 11/1979 | Stolfo | 428/420 |
| 4,420,397 | 12/1983 | Kaneko et al. | 435/262 |
| 4,485,016 | 11/1984 | Hopkins | 435/262 |
| 4,623,465 | 11/1986 | Klibanov | 435/262 |
| 4,647,952 | 3/1987 | Pokora et al. | 503/225 |

OTHER PUBLICATIONS

Atlow et al., *Dephenolization of Industrial Wastewaters*, Biotech. & Bioengin., vol. 26, pp. 599–603, 1984.
Danner et al., *The Oxidation of Phenol and Its Rxn . . .*, Archives of Biochem. Biophys., 156, pp. 759–763, 1973.
Klibanov et al., "Enzymatic Removal of Toxic Phenols and Analines from Waste Waters", Journal of App. Biochem., 2, pp. 414–421, 1980.
Alberti et al., "Enzymatic Removal of Dissolved Aromatics from Industrial Aqueous Effluents", *Biotechnology and Bioengineering Symp.*, No. 11, pp. 373–379, 1981.

Primary Examiner—David M. Naff
Assistant Examiner—Mike Meller
Attorney, Agent, or Firm—Thompson, Hine & Flory

[57] ABSTRACT

A method for treating a suspension of a phenolic resin containing residual phenols comprising the step of adding a peroxidase enzyme and a peroxide material or an oxidase enzyme and an oxygen material to said suspension to polymerize said residual phenolic monomer, and the purified suspension produced thereby is disclosed. The inventive method is used to pretreat a suspension containing a phenolic material so that the suspension may be subsequently used in a commercial process, such as the production of paper.

3 Claims, No Drawings

PRETREATMENT OF PHENOLIC RESIN SUSPENSION TO REMOVE RESIDUAL PHENOL

BACKGROUND OF THE INVENTION

The present invention relates to a process for purifying a suspension containing a phenolic resin, and more particularly, to a process for polymerizing residual monomeric phenol maintained in the solution.

BRIEF DESCRIPTION OF THE PRIOR ART

Phenolic resins have achieved a great deal of commercial use. The resins are used in such applications as color developers for carbonless copy systems, coating materials for paper, photoresist compositions for use in the production of semiconductor chips, and in the production of resins and plastics.

The phenolic resins used for the above applications are typically purchased commercially in the form of an aqueous suspension. Although such commercial suspensions have achieved a great deal of success, the suspensions can be problematical in that they contain undesirable residual phenolic monomer. Phenolic materials, particularly monomeric phenols are toxic materials which can be dangerous to both animal and plant life. For example, phenols are toxic to fish at levels above 2 mg/liter, and can be tasted in fish flesh at concentrations much lower than the toxic level. Phenols also have a relatively high biological oxygen demand (BOD) and hence, in sufficient concentrations, can deplete the oxygen in a receiving body of water. Many phenols have been declared to be hazardous pollutants. Therefore, removal of these chemicals from aqueous suspensions is of great practical significance.

In the field of industrial waste pollution control, the treatment of phenol material contained in industrial waste water has been of primary concern. Processes have included extraction, adsorption on activated carbon, steam distillation, bacterial and chemical oxidation, electrochemical techniques, and irradiation. All of these methods, although feasible and useful, suffer from one or many drawbacks such as high cost, incompleteness of purification, formation of hazardous by-products, or low efficiency.

Klibanov et al., in their article "Enzymatic Removal of Toxic Phenols and Anilines From Waste Waters", *Journal of App. Biochem.*, 2, pp. 414–421, 1980, proposes to add an amount of horseradish peroxidase enzyme and hydrogen peroxide solution to industrial waste water to polymerize the monomeric phenol into a polymer material. This is significant because the phenolic polymers, in contrast to their monomeric precursors, are practically insoluble in water. This makes them easy to remove from waste water streams.

Although the above described process has been successfully used to remove phenols from industrial waste water, no solution has been proposed to treat suspensions containing phenolic resins prior to use in an industrial process. For example, when forming paper, a phenolic resin, in suspension form, is typically added to the wet end of a paper machine to form a resin-impregnated web. Unless the suspension is pretreated to eliminate the residual phenol, the residual monomer, being soluble in nature, can pass through the paper making machine and into the industrial waste water. Accordingly, if it were possible to treat the suspension prior to use in paper-making, or any other industrial process, there would be no need to subsequently treat the industrial waste water.

Further, another concern, particularly when pretreating a suspension containing a phenolic resin is to not alter the chemical or physical properties of the resin material. If the resin is altered as a result of a pretreating purification process, its ability to perform in an industrial process cannot accurately be predicted. As the reliability and stability of the phenolic resin must be maintained at a constant to guarantee satisfactory industrial performance, steps must be taken to prevent any alteration of the resin.

U.S. Pat. No. 4,647,952 discloses phenolic developer resins. The resin, which takes the form of a combination of di-, tri-, and polyphenols, is produced by polymerizing a monomeric phenolic material by addition of a peroxidase enzyme and a peroxide or an oxidase enzyme and an oxygen material. In the preferred embodiment, the enzyme is horseradish peroxidase, and the peroxide is an aqueous hydrogen peroxide solution. This reference does not teach the pretreatment of a suspension containing a phenolic resin and residual phenolic monomer to polymerize the residual monomer for subsequent separation prior to industrial use.

Accordingly, there exists a need in the art to develop a process for purifying a suspension containing a phenolic resin without altering the resin.

SUMMARY OF THE INVENTION

In accordance with the present invention, a simple, cost-efficient method for purifying a suspension containing a phenolic resin having residual phenols is provided. The method is characterized by adding to the suspension a peroxidase enzyme and a peroxide material or an oxidase enxyme and an oxygen material to cause polymerization of the monomeric phenols to render them water insoluble.

In accordance with one embodiment of the present invention, a process for treating a suspension of a phenolic resin containing residual phenols is provided. The process includes the step of adding a peroxidase enzyme and a peroxide material or an oxidase enzyme and an oxygen material to the suspension to polymerize the residual phenols. Once the residual phenols have polymerized, they may be easily isolated and removed from the suspension by means known in the art, such as filtering, if necessary.

In practice, the preferred enzyme for use is horseradish peroxidase, and the preferred peroxide material is an aqueous solution containing hydrogen peroxide.

Another embodiment of the present invention provides a purified suspension containing a phenolic resin wherein the purification is conducted by the above-described process. Once the suspension has been purified, the suspension may then be used in a commercial process, such as in the formation of paper.

DETAILED DESCRIPTION OF THE PREFERRED EMBODIMENTS

While describing the preferred embodiments, specific terminology will be utilized for the sake of clarity. It is to be understood that such terminology includes not only the recited embodiments, but all technical equivalents which perform substantially the same function in substantially the same way to obtain the same result.

The inventive process is useful in purifying and removing phenols from commercially obtained suspensions containing a phenolic resin. These suspensions are characterized by maintaining a dispersion of phenolic resin, typically containing amounts of dimer, trimer, and polymer in a continuous phase, typically an aqueous solution. The suspension also contains an amount of residual phenolic material dissolved in the continuous phase. The residual phenolic material is maintained in a monomeric form.

Prior to use in an industrial process such as the formation of paper, the commercially available suspensions are purified in accordance with the present invention. This involves the addition of a peroxidase enzyme and a peroxide material or an oxidase enzyme and an oxygen material to the suspension prior to the suspension's initial use. For use as a peroxidase enzyme, horseradish peroxidase is preferred. However, other peroxidase enzymes such as lactoperoxidase, chloroperoxidase and bacterial peroxidases may be practiced within the scope of the present invention. For an oxidase enzyme, enzymes such as fungul laccase may be used. The peroxidase or oxidase enzyme is added to the suspension in the amount of about 10,000 to 5 mg enzyme per 100 grams of resin.

Also added to the suspension is a peroxide material or oxygen material. In practice, the peroxide material typically takes the form of hydrogen peroxide and is added in a 3% aqueous solution. Other potentially useful peroxides include methyl peroxide, etc. Approximately 0.1 to about 2.5 moles of hydrogen peroxide are added per 100 grams of resin.

The addition of the peroxidase or oxidase enzyme and the peroxide or oxygen material to the suspension preferably occurs at ambient temperatures, typically ranging between about 5° C. to about 30° C.

The addition of the peroxidase or oxidase enzyme and the peroxide or oxygen material to the suspension causes polymerization of the residual phenolic monomer dissolved in the continuous phase. In effect, this causes the phenolic material to be transformed from a water-soluble material into a water-insoluble material. Because the phenolic resin in suspension is already maintained in a polymeric form, it does not further polymerize upon contact with the peroxidase enzyme and peroxide material. Accordingly, the addition of the peroxidase enzyme and peroxide material functions solely to react with the monomeric phenol material, and not react with the phenolic resin. This is critical, as any chemical or physical alteration of the phenolic resin could significantly limit its use for certain chemical and industrial processes.

Once the peroxidase enzyme and peroxide material have been added to the suspension to polymerize the monomeric phenol, the polymerized phenol may be removed from solution by means known in the art, if desired. Examples of such means include, but are not limited to, gravity filtration, vacuum filtration, centrifuging, and the like. When performing the filtering step, care must be taken to insure that the filtering only isolates the just polymerized phenolic material from the remainder of the suspension and not filter out both the just polymerized phenolic material and the phenolic resin which is intended for subsequent use. This may be accomplished by means known in the art such as selecting specific filter sizes. Alternatively, since the residual phenols have been polymerized, they may be left in the suspension without running a significant risk of fouling machinery and the like.

Once the phenolic material has been polymerized, and optionally isolated, the suspension may then be commercially used. This provides a significant advantage as compared to using a suspension containing residual monomer because the purified suspension will not foul the machinery used during processing. Moreover, once processing is completed, the waste water produced as a result of the process will not be contaminated with monomeric phenolic material. This affords a great benefit in that no post processing purification need be performed.

It is particularly envisioned that the purified suspension be used in the production of paper, as a coating material containing a developer material for carbonless copying systems, and as a coating material for a photoresist material.

The invention is illustrated in more detail by the following non-limiting example.

EXAMPLE

Two grams of commercially obtained phenolic resin are dispersed in two liters of distilled water. The amount of residual phenol in the suspension was measured to be 56,790 micrograms per liter of water. While stirring, 0.19 grams of Sigma Type I horseradish peroxidase enzyme, and 220 milliliters of 3% hydrogen peroxide solution were added to the suspension at 20° C. While continuing stirring, the horseradish peroxidase and hydrogen peroxide solution were allowed to react with the residual phenolic monomer in suspension for a period of three hours. Thereafter, the suspension was filtered through a 0.45 micron Millipore filter to remove the polymerized residual phenol from the suspension. The resulting suspension was fixed with phosphoric acid and copper sulfate in accordance with United States Environmental Protection Agency procedures to measure the amount of residual phenol in the suspension. The measured amount was 27.3 micrograms per liter.

The treated suspension was then used to produce hand sheets utilizing known paper-making procedures. The produced hand sheets using the purified suspension were subsequently evaluated for performance. The performance obtained was satisfactory.

Having described the invention in detail, and by reference to the preferred embodiment thereof, it will be apparent that modifications and variations are possible without departing from the scope of the invention defined in the appended claims.

What is claimed is:

1. A method for treating a suspension of a phenolic resin to render said suspension essentially free of unpolymerized phenolic monomer, said method comprising the steps of:

adding a perioxidase enzyme and a perioxide to a suspension of a phenolic resin containing residual phenolic monomer to thereby polymerize said residual phenolic monomer and render said monomer insoluble in water, said polymerized monomer being retained in said suspension.

2. The method according to claim 1 wherein said enzyme comprises a peroxide enzyme, and wherein said peroxidase enzyme is horseradish perioxidase.

3. The method according to claim 2 wherein said perioxide material is an aqueous hydrogen peroxide solution.

* * * * *

UNITED STATES PATENT AND TRADEMARK OFFICE
CERTIFICATE OF CORRECTION

PATENT NO. : 5,110,740
DATED : May 5, 1992
INVENTOR(S) : Alexander R. Pokora and John J. Stolfo It is certified that error appears in the above-identified patent and that said Letters Patent is hereby corrected as shown below:

Column 4, Line 55, change "perioxidase" to --peroxidase--

Column 4, Line 55, change "perioxide" to --peroxide--

Column 4, Line 63, change "perioxidase" to --peroxidase--

Column 4, Line 65, change "perioxide" to --peroxide--

Signed and Sealed this

Thirty-first Day of August, 1993

Attest:

BRUCE LEHMAN

*Attesting Officer*  *Commissioner of Patents and Trademarks*